(12) United States Patent
Eisele et al.

(10) Patent No.: US 10,781,421 B2
(45) Date of Patent: Sep. 22, 2020

(54) CELLULAR TEST SYSTEMS FOR THE DETERMINATION OF THE BIOLOGICAL ACTIVITIES OF NEUROTOXIN POLYPEPTIDES

(71) Applicant: MERZ PHARMA GmbH & CO. KGaA, Frankfurt am Main (DE)

(72) Inventors: Karl-Heinz Eisele, Frankfurt am Main (DE); Kai Harting, Frankfurt am Main (DE)

(73) Assignee: MERE PHARMA GmbH & CO. KGaA, Frankfurt am Main (DE)

( * ) Notice: Subject to any disclaimer, the term of this patent is extended or adjusted under 35 U.S.C. 154(b) by 0 days.

(21) Appl. No.: 16/144,059

(22) Filed: Sep. 27, 2018

(65) Prior Publication Data

US 2019/0032009 A1 Jan. 31, 2019

Related U.S. Application Data

(62) Division of application No. 14/435,583, filed as application No. PCT/EP2013/071456 on Oct. 15, 2013, now Pat. No. 10,125,350.

(60) Provisional application No. 61/714,282, filed on Oct. 16, 2012.

(30) Foreign Application Priority Data

Oct. 16, 2012 (EP) ..................... 12188662

(51) Int. Cl.
| | |
|---|---|
| G01N 33/50 | (2006.01) |
| G01N 33/573 | (2006.01) |
| C12N 5/0793 | (2010.01) |

(52) U.S. Cl.
CPC ....... *C12N 5/0619* (2013.01); *G01N 33/5058* (2013.01); *G01N 33/573* (2013.01); *C12N 2500/32* (2013.01); *C12N 2500/36* (2013.01); *C12N 2500/38* (2013.01); *C12N 2500/60* (2013.01); *C12N 2501/06* (2013.01); *C12N 2506/30* (2013.01); *G01N 2333/952* (2013.01)

(58) Field of Classification Search
CPC .............. A61K 38/4893; A61K 9/0019; A61K 2039/5152; G01N 2333/952; C12N 2500/60; C12N 2506/30
See application file for complete search history.

(56) References Cited

U.S. PATENT DOCUMENTS

| | | |
|---|---|---|
| 2006/0216821 A1 | 9/2006 | Totey et al. |
| 2007/0155012 A1 | 7/2007 | Privat |
| 2010/0233802 A1* | 9/2010 | Zhu .................. C12N 5/0618 435/325 |
| 2012/0149106 A1 | 6/2012 | Zhu |
| 2014/0093957 A1 | 4/2014 | Zhu |
| 2014/0248644 A1* | 9/2014 | Wang ................. C12Q 1/37 435/7.94 |

FOREIGN PATENT DOCUMENTS

| | | |
|---|---|---|
| WO | WO2009114748 | 9/2009 |
| WO | WO 2010/085473 | 7/2010 |
| WO | WO2010105234 | 9/2010 |
| WO | WO2011096728 | 8/2011 |
| WO | WO2012123370 | 9/2012 |
| WO | WO2013131991 | 9/2013 |

OTHER PUBLICATIONS

Tsukamoto et al., Microbiol Immunol, 56:664-672, published Jun. 27, (Year: 2012).*
Certificate of Analysis, Neurobasal medium according to Thermo Fisher Scientific Specifications, published by Gibco Sep. 2019. (Year: 2019).*
International Search Report for PCT/EP2013/071456 dated Mar. 17, 2014.
Arnon, Stephen, S., et al., JAMA, Feb. 28, 2001 vol. 285, No. 8, pp. 1059-1070.
Babuska, V., et al., Prague Medical Report, 2010, vol. 1.1.1, No. 4, pp. 289-299.
Brewer et al., J Neurosci Res, 35:567-576, 1993.
Couesnon, Aurelle, et al., "Expression of botulinum neurotoxins A and E, and associated non toxin genes, during the transition phase and stability at high temperature: analysis by quantitative reverse transcription-PCR" Microbiology, 2006, vol. 152, pp. 759-770.
Favaron et al., PNAS, 85:7351-7355, 1988.

(Continued)

*Primary Examiner* — Kimberly Ballard
*Assistant Examiner* — Stacey N MacFarlane
(74) *Attorney, Agent, or Firm* — Hueschen and Sage

(57) ABSTRACT

The present invention pertains to a method for the generation of neurotoxin-sensitive, neuronal differentiated cells comprising the steps of: a) cultivating tumor cells which are able to differentiate into neuronal cells in a culture medium under conditions and for a time which primes said tumor cells for neuronal differentiation; and b) cultivating the tumor cells primed for neuronal differentiation of a) in a differentiation medium having an osmolality of 100 to 270 mOsm/kg, and comprising (i) B27 supplement and/or (ii) N2 supplement, for at least 3 days, thereby obtaining neurotoxin-sensitive, neuronal differentiated cells. The invention further relates to neurotoxin-sensitive, neuronal differentiated cells obtainable by the method of the invention. In addition, the invention encompasses a method for determining the activity of a neurotoxin polypeptide comprising the steps of: a) contacting the neurotoxin-sensitive, neuronal differentiated cells obtainable by the method of the invention with a neurotoxin polypeptide; b) cultivating the neurotoxin-sensitive, neuronal differentiated cells of step a) for 3 to 74 hours or 72 hours under conditions which allow for the neurotoxin polypeptide to exert its biological activity; and c) determining the activity of the neurotoxin polypeptide in the said cells after cultivation according to step b). Finally, the invention provides for a medium comprising OptiMEM, FBS, B27 supplement, and N2 supplement.

13 Claims, No Drawings

(56) References Cited

OTHER PUBLICATIONS

Fernandez-Salas, Ester, et al., "Botulinum neurotoxin serotype A specific cell-based potency assay to replace the mouse bioassay", PLOS one, Nov. 2012, vol. 7, Issue 11, e49516, pp. 1-13.
Fischer, Audrey, et al., "Single molecule detection of intermediates during botulinum neurotoxin translocation across membranes", PNAS, Jun. 19, 2007, vol. 104, No. 25, pp. 10447-10452.
Gimenez-Cassina, Alredo, et al., "Differentiation of a human neuroblastoma into neuron-like cells increases their susceptibility to transduction by herpesviral vectors", Journal of Neuroscience Research, 2006, vol. 84, pp. 755-767.
International Search Report for application PCT/EP2013/071456 dated Mar. 17, 2014.
IPRP from application PCT/EP2013/071456 dated Apr. 30, 2015.
Jost, Wolfgang, H., et al., "Botulinum neurotoxin type A free of complexing proteins (XEOMIN) in focal dystonia", Drugs, 2007, vol. 67, No. 5, pp. 669-683.
Khoo, Melissa, L. M., et al., "Transplantation of neuronal-primed human bone marrow mesenchymal stem cells in hemiparkinsonian rodents", PLOS one, May 2011, vol. 6, Issue 5, e19025, pp. 1-16.
Krieglstein, Kerstin, et al., "Arrangement of disulfide bridges and positions of sulfhydryl groups in tetanus toxin", Eur. J. Biochem., 1990, vol. 188, pp. 39-45.
Krieglstein, Kerstin, G., et al., "Limited proteolysis of tetanus toxin", Eur. J. Biochem., 1991, vol. 202, pp. 41-51.
Krieglstein, Kerstin, G., et al., "Covalent structure of botulinum neurotoxin type A: location of sulfhydryl groups, and disulfide bridges and identification of C-termini of light and heavy chains", Journal of Protein Chemistry, 1994, vol. 13, No. 1, pp. 49-57.
Marini, Patrizia, et al., "SiMa, a new neuroblastoma cell line combining poor prognostic cytogenetic markers with high adrenergic differentiation", Cancer Genet. Cytogenet., 1999, vol. 112, pp. 161-164.
Mcburney, Michael, W., et al., "Isolation of male embryonal carcinoma cells and their chromosome replication patterns", Developmental Biology, 1982, vol. 80, pp. 503-508.
Migliore, Michele, et al., "An integrated approach to classifying neuronal phenotypes", Nature, Oct. 2005, vol. 6, pp. 810-818.
Monzo et al., J Neurosci Methods, 204:87-103, 2011.
Nat, Roxana, et al., "Neurogenic neuroepithelial and radial glial cells generated from six human embryonic stem cell lines in serum-free suspension and adherent cultures", GLIA, 2007, vol. 55, pp. 385-399.
Office Action from EP13779189.3 dated Apr. 12, 2016.
Pellett, Sabine, et al., "Sensitive and quantitative detection of botulinumm neurotoxin in neurons derived from mouse embryonic stem cells", Biochem Biophys Res Commun., Jan. 4, 2011 vol. 404, No. 1, pp. 388-392.
Rudnicki, Michael, A., et al., "Actin and myosin expression during development of cardiac muscle from cultured embryonal carcinoma cells", Developmental Biology, 1990, vol. 138, pp. 348-358.
Shafer et al., NeuroToxicology, 12:473-492, 1991.
Sidell, N., Journal of the Natl Cancer Inst., 68:589-596, 1981.
Sigma Product Information Sheet R5382, RPMI-1640 Medium, published Sep. 1998.
Silberstein, Stephen, "Botulinum neurotoxins: origins and basic mechanisms of action",Pain Practice, 2004, vol. 4, Issue 1S, pp. 319-326.
Steindler, Dennis, A., "Stem cells, regenerative medicine, and animal models of disease", ILAR Journal, 2007, vol. 48, No. 4, pp. 323-338.
Straughan, Donald, W., "Progress in applying the three Rs to the potency testing of botulinum toxin type A" ATLA, 2006, vol. 34, pp. 305-313.
ThermoFisher B-27 Description, Nov. 2, 2015. [online] Retrived from <https://web-beta.archive.org/web/20151102022700/https://www.thermofisher.com/order/catalog/product/12587010> Retrieved on Apr. 26, 2017.
Vazey, Elena, M., et al., "Differential fate and functional outcome of lithium chloride primed adult neural progenitor cell transplants in a rat model of Huntington disease", Stem Cell Research & Therapy, 1010, vol. 1, No. 41, pp. 1-11.
Whitemarsch, Regina, C. M., et al., "Novel application of human neurons derived from induced pluripotent stem cells for highly sensitive botulinum neurotoxin detection", Toxicological Sciences, 2012, vol. 126, No. 2, pp. 426-435.
Whitemarsh, et al. Biochem Biophys Res Commun., 427(2):426-430, published online Sep. 20, 2012.
Yao, M., et al., "Neuronal differentiation of P19 embryonal carcinoma cells in defined media", Journal Neuroscience Research, 41, 1995, pp. 792-804.

\* cited by examiner

CELLULAR TEST SYSTEMS FOR THE DETERMINATION OF THE BIOLOGICAL ACTIVITIES OF NEUROTOXIN POLYPEPTIDES

The present invention pertains to a method for the generation of neurotoxin-sensitive, neuronal differentiated cells comprising the steps of: a) cultivating tumor cells which are able to differentiate into neuronal cells in a culture medium under conditions and for a time which primes said tumor cells for neuronal differentiation; and b) cultivating the tumor cells primed for neuronal differentiation of a) in a differentiation medium having an osmolality of 100 to 270 mOsm/kg, and comprising (i) B27 supplement and/or (ii) N2 supplement, for at least 3 days, thereby obtaining neurotoxin-sensitive, neuronal differentiated cells. The invention further relates to neurotoxin-sensitive, neuronal differentiated cells obtainable by the method of the invention. In addition, the invention encompasses a method for determining the activity of a neurotoxin polypeptide comprising the steps of: a) contacting the neurotoxin-sensitive, neuronal differentiated cells obtainable by the method of the invention with a neurotoxin polypeptide; b) cultivating the neurotoxin-sensitive, neuronal differentiated cells of step a) for 3 to 74 hours or 72 hours under conditions which allow for the neurotoxin polypeptide to exert its biological activity; and c) determining the activity of the neurotoxin polypeptide in the said cells after cultivation according to step b). Finally, the invention provides for a medium comprising OptiMEM, FBS, B27 supplement, and N2 supplement.

*Clostridium botulinum* and *Clostridium tetani* produce highly potent neurotoxins, i.e. botulinum toxins (BoNTs) and tetanus toxin (TeNT), respectively. These Clostridial neurotoxins (CNTs) specifically bind to neuronal cells and disrupt neurotransmitter release. Each toxin is synthesized as an inactive unprocessed approximately 150 kDa single-chain protein. The posttranslational processing involves formation of disulfide bridges, and limited proteolysis (nicking) by the bacterial protease(s). Active neurotoxin consists of two chains, an N-terminal light chain of approx. 50 kDa and a heavy chain of approx. 100 kDa linked by a disulfide bond. CNTs structurally and functionally consist of three domains, i.e. the catalytic light chain, the heavy chain encompassing the translocation domain (N-terminal half) and the receptor binding domain (C-terminal half); see, e.g., Krieglstein 1990, Eur. J. Biochem. 188, 39; Krieglstein 1991, Eur. J. Biochem. 202, 41; Krieglstein 1994, J. Protein Chem. 13, 49. The Botulinum neurotoxins are synthesized as molecular complexes comprising the 150 kDa neurotoxin protein and associated non-toxic proteins. The complex sizes differ based on the Clostridial strain and the distinct neurotoxin serotypes ranging from 300 kDa, over 500 kDa, and 900 kDa. The non-toxic proteins in these complexes stabilize the neurotoxin and protect it against degradation; see Silberstein 2004, Pain Practice 4, S19-S26.

*Clostridium botulinum* secretes seven antigenically distinct serotypes designated A to G of the botulinum neurotoxin (BoNT). All serotypes together with the related tetanus neurotoxin (TeNT) secreted by *Clostridium tetani*, are $Zn^{2+}$-endoproteases that block synaptic exocytosis by cleaving SNARE proteins; see Couesnon, 2006, Microbiology, 152, 759. CNTs cause the flaccid muscular paralysis seen in botulism and tetanus; see Fischer 2007, PNAS 104, 10447.

Despite its toxic effects, botulinum toxin complex has been used as a therapeutic agent in a large number of diseases. Botulinum toxin serotype A was approved for human use in the United States in 1989 for the treatment of strabism, blepharospasm, and other disorders. It is commercially available as Botulinum toxin A (BoNT/A) protein preparation, for example, under the trade name BOTOX (Allergan, Inc.) or under the trade name DYSPORT/RELOXIN (Ipsen, Ltd). An improved, complex-free Botulinum toxin A preparation is commercially available under the trade name XEOMIN (Merz Pharmaceuticals, GmbH). For therapeutic applications, the preparation is injected directly into the muscle to be treated. At physiological pH, the toxin is released from the protein complex and the desired pharmacological effect takes place. The effect of Botulinum toxin is only temporary, which is the reason why repeated administration of Botulinum toxin may be required to maintain a therapeutic affect.

The Clostridial neurotoxins weaken voluntary muscle strength and are effective therapy for strabism, focal dystonia, including cervical dystonia, and benign essential blepharospasm. They have been further shown to relief hemifacial spasm, and focal spasticity, and moreover, to be effective in a wide range of other indications, such as gastrointestinal disorders, hyperhidrosis, and cosmetic wrinkle correction; see Jost 2007, Drugs 67, 669.

During the manufacturing process of Clostridial neurotoxins, the qualitative and quantitative determination of said neurotoxins as well as the quality control of the biologically active neurotoxin polypeptides is of particular importance. In addition, governmental agencies accept only simple, reliable, and validated Botulinum toxin activity assays. At present the mouse $LD_{50}$ bioassay, a lethality test, remains the "gold standard" used by pharmaceutical manufacturers to analyze the potency of their preparations; see Arnon et al. (2001), JAMA 285, 1059-1070. However, in recent years, considerable effort has been undertaken to seek for alternative approaches to alleviate the need for animal testing and all the disadvantages, costs and ethical concerns associated with this type of animal-based assays. In addition, the regulatory agencies are engaging pharmaceutical companies to apply the three "Rs" principle to the potency testing of Botulinum neurotoxins: "Reduce, Refine, Replace"; see Straughan, Altern. Lab. Anim. (2006), 34, 305-313. As a consequence, cell-based test systems have been developed in order to provide reasonable alternatives to methods using live animals. Yet, only three cellular test systems are available for the determination of neurotoxin biological activity thus far which have been shown to be sufficiently sensitive to neurotoxin polypeptides. These cell-based test systems include the use of primary neurons isolated from rodent embryos which are differentiated in vitro (Pellett et al. (2011), Biochem. Biophys. Res. Commun. 404, 388-392), neuronal differentiated induced pluripotent stem cells (Whitemarsh et al. (2012), Toxicol. Sci. 126, 426-35), and a subclone of the SiMa cell line (WO 2010/105234 A1).

However, the isolation of primary neurons requires the killing of animals and is laborious and time consuming. Further, test systems using different primary neurons show large variances. Similarly, the generation of neuronal differentiated induced pluripotent stem cells is difficult and time consuming. In addition, storage of such cells is very problematic. Assays using tumor cell lines are frequently not sensitive enough to BoNT. Moreover, complex differentiation protocols are required for said tumor cell lines which result in large variances and/or high failure rates of assays using said cell lines.

In light of the above, further test systems for the determination of neurotoxin polypeptide activity acceptable to governmental agencies and providing for an alternative to animal-based test systems are highly desirable.

Thus, the technical problem underlying the present invention may be seen as the provision of means and methods complying with the aforementioned needs. The technical problem is solved by the embodiments characterized in the claims and herein below.

The present invention relates, in a first aspect, to a method for the generation of neurotoxin-sensitive, neuronal differentiated cells comprising the steps of:

a) cultivating tumor cells which are able to differentiate into neuronal cells in a culture medium under conditions and for a time which primes said tumor cells for neuronal differentiation; and b) cultivating the tumor cells primed for neuronal differentiation of a) in a differentiation medium having an osmolality of 100 to 270 mOsm/kg, and comprising (i) B27 supplement and/or (ii) N2 supplement, for at least 3 days, thereby obtaining neurotoxin-sensitive, neuronal differentiated cells.

In this method of the invention, tumor cells which are able to differentiate into neuronal cells are first grown in a cell culture medium under conditions and for a time which primes said tumor cells for neuronal differentiation. Thereafter, the tumor cells thus primed for neuronal differentiation are transferred into a differentiation medium having an osmolality of 100 to 270 mOsm/kg. Further, this differentiation medium comprises at least (i) B27 supplement and/or (ii) N2 supplement. Alternatively, the differentiation medium can comprise NS21 supplement, instead of B27 supplement and/or N2 supplement. Cultivation in said differentiation medium is carried out for at least 3 days. Thereby, neurotoxin-sensitive, neuronal differentiated cells are obtained. Preferably, the differentiation medium comprises neurobasal medium.

As a result of this novel differentiation method or protocol of the invention, neurotoxin-sensitive, neuronal differentiated cells are obtained which exhibit significantly improved sensitivity to neurotoxin polypeptides, as shown in detail in the following Example.

Clostridial neurotoxins are characterized in that they specifically inhibit the secretion of neurotransmitters from pre-synaptic nerve endings. The selectivity for peripheral neurons is mediated by the recognition of two different receptors, SV2 and GT1b. The physiological effect of the neurotoxins is based on the cleavage of a protein of the so-called SNARE complex subsequent to the binding of the receptor and the translocation of the neurotoxin's light chain. The determination of the biological activity of BoNT is an important aspect in the characterization of said neurotoxin proteins and is required, inter alia, by regulatory authorities for the clearance of BoNT-containing products. A reliable test for the measurement of the biological activity of BoNT is, therefore, basis for research, development and marketing of products containing BoNT. Furthermore, cell-based test systems shall replace the thus far predominant animal tests, for ethical reasons. For establishing such cell-based test systems, a sufficient high sensitivity of neuronal cells or cell lines towards Botulinum neurotoxins is essential. However, in order to obtain such high sensitivity, laborious differentiation methods of neuronal cell lines are required so far. As a result, only a few cell-based test systems are available yet. To determine the biological activity of Botulinum toxins in pharmaceutical products, the neuronal cells or cell lines shall have the following properties: First, the cells should be of human, neuronal origin in order to resemble the target as close as possible, i.e. the human patient. Second, the cell system shall be robust towards excipients in the final product and, preferably, also towards impurities in intermediate stages of the production process (process controls). Third, the cell-based test system shall exhibit a dynamic measuring range which allows for the accurate determination of the biological activity of BoNT in a vial (for example, 50 U BoNT/A). Considering technical factors such as the solubility of excipients, volumes of cell culture media etc., a BoNT concentration of less than 1 pM has to be determined accurately. According to the inventors' best knowledge, only three cell-based test systems are available so far which show sufficiently high sensitivity to BoNT. These include primary neurons of embryos from rodents, neuronal differentiated induced pluripotent stem cells and a subclone of the SiMa cell line, as already mentioned elsewhere herein. However, said cell lines have been reported to exhibit a sufficiently high sensitivity, only after complex and laborious differentiation protocols, which are frequently associated with large variances. In contrast, the present invention provides for a simple, reliable and robust cell-based test system for the measurement of the biological activity of Botulinum neurotoxins (BoNT) which fulfills the abovementioned requirements and which has been further improved, in comparison to the cellular test systems described in the art.

More specifically, SiMa (human neuroblastoma) and P19 (murine embryonal carcinoma) tumor cells were first cultivated as described in the prior art, then seeded on multi-well plates and primed for neuronal differentiation, as described elsewhere herein and in the following Example. In a subsequent, novel differentiation step, the cell culture medium was substituted by a differentiation medium comprising a medium having low osmolality, such as an osmolality of 100 to 270 mOsm/kg. One example for such a medium having low osmolality is neurobasal medium. After a period of differentiation (for example, 3 to 7 days) in which the medium was replaced by fresh medium, if applicable, neurotoxin polypeptide was added to the cell culture medium. Furthermore, GT1b was used as a sensitivity enhancer for BoNT in the method of the invention. For example, 50 μM GT1b was added to the neurobasal medium upon and/or prior to intoxication of the cells with neurotoxin polypeptide. After further 72 h incubation with the neurotoxin polypeptide, the cells were stopped and the biological activity of the neurotoxin polypeptide was analyzed. As a result, a significant increase in the sensitivity of said cells to BoNT has been found.

It has surprisingly found by the present inventors that the low osmolality of the differentiation medium is responsible for the increased sensitivity to BoNT of the neurotoxin-sensitive, neuronal differentiated cells produced by the methods of the invention, as demonstrated in the following Example. This finding was no trivial task as evidenced from the history of experiments which finally ended up in the methods of the invention: At the beginning, the inventors used a differentiation medium described in the art which comprised MEM+N2 supplement+B27 supplement; see differentiation medium 2, in the Example. The sensitivity of the neuronal differentiated cells to BoNT which could be achieved by this differentiation medium was about 1 to 2 pM. In the next step, it has been found that the addition of retinoic acid resulted in only a small increase in sensitivity to BoNT of the neuronal differentiated cells. In contrast, a significantly improved sensitivity by a factor of about 7 to 10 could be achieved by the use of neurobasal medium. For example, a EC50 of 0.22 picomolar ($2.18 \times 10^{-13}$ mol/l) has been found for SiMa cells when a differentiation medium comprising neurobasal medium+2% B27 supplement+1% GlutaMAX+3 micromolar retinoic acid (RA) has been used, in the method of the invention. Further, it could be shown that retinoic acid was not essential in the differentiation medium, for the improved sensitivity of the neuronal differentiated cells as long as neurobasal medium was included. Unexpectedly, the inventors could demonstrate that an improved sensitivity could even be achieved by using the differentiation medium (comprising MEM+N2 supplement+B27 supplement) described in the art which they had used at the beginning of the series of experiments if only diluted to an osmolality of 225 mOsm/kg. In contrast, the non-diluted differentiation medium containing the mentioned components had an osmolality of 300 mOsm/kg. Accordingly, the increased sensitivity to BoNT of the neurotoxin-sensitive, neuronal differentiated cells produced by the methods of the invention is a result of the low osmolality of the differentiation medium. In addition to improved sensitivity, said novel differentiation protocol of the invention showed higher precision and robustness of testing the biological activity of neurotoxin polypeptides, in comparison to methods known in the art.

As used herein, the singular forms "a", "an" and "the" include both singular and plural reference unless the context clearly dictates otherwise. By way of example, "a cell" refers to one or more than one cell.

As used herein, the term "about" when qualifying a value of a stated item, number, percentage, or term refers to a range of plus or minus 10 percent, 9 percent, 8 percent, 7 percent, 6 percent, 5 percent, 4 percent, 3 percent, 2 percent or 1 percent of the value of the stated item, number, percentage, or term. Preferred is a range of plus or minus 10 percent.

The terms "comprising", "comprises" and "comprised of" as used herein are synonyms with "including", "includes" or "containing", "contains", and are inclusive or open-ended and do not exclude additional, non-recited members, elements or method steps. Evidently, the term "comprising" encompasses the term "consisting of". More specifically, the term "comprise" as used herein means that the claim encompasses all the listed elements or method steps, but may also include additional, unnamed elements or method steps. For example, a method comprising steps a), b) and c) encompasses, in its narrowest sense, a method which consists of steps a), b) and c). The phrase "consisting of" means that the composition (or device, or method) has the recited elements (or steps) and no more. In contrast, the term "comprises" can encompass also a method including further steps, e.g., steps d) and e), in addition to steps a), b) and c).

In case numerical ranges are used herein such as "retinoic acid in a concentration between 0.1 and 0.5 micromolar", the range includes not only 0.1 and 0.5 micromolar, but also any numerical value in between 0.1 and 0.5 micromolar, for example, 0.2, 0.3 and 0.4 micromolar.

The term "in vitro" as used herein denotes outside, or external to, the animal or human body. The term "in vitro" as used herein should be understood to include "ex vivo". The term "ex vivo" typically refers to tissues or cells removed from an animal or human body and maintained or propagated outside the body, e.g., in a culture vessel. The term "in vivo" as used herein denotes inside, or internal to, the animal or human body.

The term "neurotoxin-sensitive cell" as used herein means a cell which is susceptible to a neurotoxin polypeptide exhibiting the biological properties characteristic for a neurotoxin polypeptide, namely, (a) receptor binding, (b) internalization, (c) translocation across the endosomal membrane into the cytosol, and/or (d) endoproteolytic cleavage of proteins involved in synaptic vesicle membrane fusion. Accordingly, a "neurotoxin-sensitive cell" as referred to herein is susceptible to neurotoxin intoxication. More specifically, "susceptible to neurotoxin intoxication" as denoted herein means a cell that can undergo the overall cellular mechanisms whereby a neurotoxin polypeptide (e.g., BoNT/A) cleaves a neurotoxin substrate (e.g., the BoNT/A substrate SNAP-25) and encompasses the binding of the neurotoxin to its corresponding receptor (e.g., binding of BoNT/A to BoNT/A receptor), the internalization of the neurotoxin/receptor complex, the translocation of the neurotoxin light chain from an intracellular vesicle into the cytoplasm, and the proteolytic cleavage of the neurotoxin substrate. Assays for determining the biological activity of a neurotoxin polypeptide are well known in the art and also described elsewhere herein (see, e.g., Pellett et al., Withemarsh et al. Toxicological Sciences 126(2), 426-435 (2012), WO 2010/105234 A1) As appreciated by those skilled in the art, the neurotoxin-sensitive cell is preferably able to first uptake a neurotoxin and then undergoes the overall cellular mechanisms listed above. A neurotoxin-sensitive cell as used herein can uptake, e.g., about 100 nanomolar (nM), about 10 nM, about 1 nM, about 500 picomolar (pM), about 400 pM, about 300 pM, about 200 pM, about 100 pM, about 90 pM, about 80 pM, about 70 pM, about 60 pM, about 50 pM, about 40 pM, about 30 pM, about 20 pM, about 10 pM, about 9 pM, about 8 pM, about 7 pM, about 6 pM, about 5 pM, about 4 pM, about 3 pM, about 2 pM, about 1 pM, about 0.5 pM, or about 0.1 pM of neurotoxin polypeptide or even less than one of the indicated values. EC50 values above 100 pM have been reported in the literature. By definition, a cell susceptible to neurotoxin intoxication must express, or be engineered to express, at least one neurotoxin receptor and at least one neurotoxin substrate. Receptors and substrates for neurotoxins are described in the art. Accordingly, said cell is preferably susceptible to a biologically active or mature neurotoxin polypeptide as defined herein. The term "neurotoxin-sensitive cell" as used herein comprises a cell or a cell line, for example, an isolated, primary cell or a cell line thereof or a cell of an established cell line or an established cell line, preferably a neuroblastoma cell or neuroblastoma cell line as defined herein. Preferably, the "neurotoxin-sensitive cell" as used herein is susceptible to neurotoxin intoxication by, e.g., about 1 nM or less, 500 pM or less, about 400 pM or less, about 300 pM or less, about 200 pM or less, about 100 pM or less, about 90 pM or less, about 80 pM or less, about 70 pM or less, about 60 pM or less, about 50 pM or less, about 40 pM or less, about 30 pM or less, about 20 pM or less, about 10 pM or less, about 9 pM or less, about 8 pM or less, about 7 pM or less, about 6 pM or less, about 5 pM or less, about 4 pM or less, about 3 pM or less, about 2 pM or less, about 1 pM or less, about 0.9 pM or less, about 0.8 pM or less, about 0.7 pM or less, about 0.6 pM or less, about 0.5 pM or less, about 0.4 pM or less, about 0.3 pM or less, about 0.2 pM or less, or even about 0.1 pM or less. For example, an extremely low EC50 value of less than 0.1 pM has been reached for SiMa cells and an EC50 of less than 1 pM for P19 cells, by using the novel differentiation method of the present invention. As known in the art, the "half maximal effective concentration (EC50)" refers to the concentration of a drug, antibody or toxicant which induces a response halfway between the baseline and maximum after some specified exposure time. It is commonly used as a measure of drug's potency. The EC50 of a graded dose response curve therefore represents the concentration of a compound where 50% of its maximal effect is observed. The EC50 of a quantal dose response curve represents the concentration of a compound where 50% of the population exhibits a response, after a specific exposure duration.

Methods for the identification of cells or cell lines susceptible to neurotoxin intoxication and/or having neurotoxin uptake capacity, i.e. neurotoxin-sensitive cells as defined herein, are known in the art; see, e.g. US 2012/0122128 A1. The biological activity of the neurotoxin polypeptides, in an aspect, results from all of the aforementioned biological properties. Only a few cell-based assays with sufficient high sensitivity towards neurotoxins which can be used for the determination of the biological activity of a neurotoxin have been described in the prior art so far, as indicated elsewhere herein. In vivo assays for assessing the biological activity of neurotoxins include, for example, the already mentioned mouse $LD_{50}$ assay and the ex vivo mouse hemidiaphragm assay as described by Pearce et al. and Dressier et al.; see Pearce 1994, Toxicol. Appl. Pharmacol. 128: 69-77 and Dressier 2005, Mov. Disord. 20:1617-1619. The methods of the invention provide for a simple, reliable, and robust cell-based test system with increased sensitivity to neurotoxin polypeptides, in comparison to the cellular test systems described in the art which require complex differentiation protocols. Accordingly, the methods of the invention provide for an improved alternative to the cellular test systems or animal tests of the art for determining the biological activity of neurotoxins. As known to those skilled in the art, the biological activity of neurotoxins is commonly expressed in Mouse Units (MU). One MU is the amount of neurotoxic component, which kills 50% of a specified mouse population after intraperitoneal injection, i.e. the mouse i.p. LD 50.

The terms "differentiation", "differentiating" or "differentiated" as used herein denote the process by which an unspecialized or a relatively less specialized cell becomes relatively more specialized. In the context of cell ontogeny, the adjective "differentiated" is a relative term. Hence, a "differentiated cell" is a cell that has progressed further down a certain developmental pathway than the cell it is being compared with. A differentiated cell may, for example, be a terminally differentiated cell, i.e., a fully specialized cell that takes up specialized functions in various tissues and organs of an organism, and which may but need not be post-mitotic. In another example, a differentiated cell may also be a progenitor cell within a differentiation lineage, which can further proliferate and/or differentiate. Similarly, a cell is "relatively more specialized" if it has progressed further down a certain developmental pathway than the cell it is being compared with, wherein the latter is therefore considered "unspecialized" or "relatively less specialized". A relatively more specialized cell may differ from the unspecialized or relatively less specialized cell in one or more demonstrable phenotypic characteristics, such as, for example, the presence, absence or level of expression of particular cellular components or products, e.g., RNA, proteins, specific cellular markers or other substances, activity of certain biochemical pathways, morphological appearance, proliferation capacity and/or kinetics, differentiation potential and/or response to differentiation signals, etc., wherein such characteristics signify the progression of the relatively more specialized cell further along the said developmental pathway.

The term "neuronal differentiated cell" as used herein means a cell which has reached the final neuronal differentiation status. For example, the murine embryonic carcinoma cells P19 cells which have been used in the method of the present invention differentiate first to neuroprogenitor cells before they further differentiate to neurons. The neurodifferentiation process can be followed, e.g., phenotypically (by phase contrast microscopy) and/or by the expression of neuronal differentiation markers; see, e.g., Babuska et al. (2010), Prague Medical Report 111, 289-299 or Migliore and Shepherd, Nature Reviews Neuroscience 6, 810-818 (2005). Assays which can be used for the determination of the expression of said neuronal differentiation markers include, for example, PCR, RT-PCR, Northern blot, Western blot or Dot blot, immunoprecipitation analysis, enzyme-linked immunosorbent analysis (ELISA) or FACS analysis which are known in the art; see, e.g., Sambrook, Molecular Cloning: A Laboratory Manual, Cold Spring Harbor Laboratory, third edition, 2001. Assays for testing the further characteristics of neuronal differentiated cells are also known in the art.

The term "tumor cells which are able to differentiate into neuronal cells" as used herein means, for example, neuroblastoma cells, embryonic carcinoma cells, teratocarcinoma cells, neural hybrid cells (e.g. neuron x glioblastoma cells), or fibroblastoma cells. The methods of the invention have been exemplified using mouse and human tumor cells, i.e. P19 (murine embryonic carcinoma) and SiMa (human neuroblastoma) cells, respectively.

The term "neuroblastoma" as used herein means a cancer that develops from nerve cells found in several areas of the body. Neuroblastoma most commonly arises in and around the adrenal glands, which have similar origins to nerve cells and sit atop the kidneys. However, neuroblastoma can also develop in other areas of the abdomen and in the chest, neck and pelvis, where groups of nerve cells exist. The term "neuroblastoma cell" as used herein comprises one or more neuroblastoma cells which are neurotoxin-sensitive and capable of differentiating to neuronal cells. The neuroblastoma cell can be a primary neuroblastoma cell or a primary neuroblastoma cell line. Encompassed by said term are also established neuroblastoma cells or cell lines. The neuroblastoma cell can be a mammalian neuroblastoma cell, for example, a rodent neuroblastoma cell such as a rat or mouse neuroblastoma cell, but also a monkey neuroblastoma cell, such as a rhesus, macaque, or cynomolgus neuroblastoma cell or a primate neuroblastoma cell such as a chimpanzee neuroblastoma cell or, preferably, a human neuroblastoma cell. Examples of established neuroblastoma cell lines encompass, e.g., Neuro-2a (mouse neuroblastoma), Kelly (human neuroblastoma), SH-SYSY (human neuroblastoma) or SiMa (human neuroblastoma). Human neuroblastoma cells are preferably used in the methods of the invention in order to generate neurotoxin-sensitive, neuronal differentiated cells. More preferably, the neuroblastoma cell as defined herein is a SiMa cell or SiMa cell line. This is because SiMa cells are easy to transfer, in a BoNT-sensitive form. In addition, they have high sensitivity to BoNT. Moreover, the differentiation protocol for SiMa cells is simple and rather short, in comparison to other neuroblastoma cells or cell lines. The SiMa cells as used in the method of the invention can be parental SiMa cells or (sub)clones derived therefrom.

In step a) of the aforementioned method of the invention, "cultivating" means cultivation of the tumor cells which are able to differentiate into neuronal cells as defined herein in a cell culture medium under conditions and for a time which primes said tumor cells for neuronal differentiation. The term "priming" as used in cellular differentiation processes, is known in the art; see, e.g. Khoo et al., PLOS ONE 6(5): e19025, (2011); Steindler, ILAR Journal 48(4), 323-338 (2007); Vazey and Connor, Stem Cell Research & Therapy 1: 41 (2010). "Priming the tumor cells for neuronal differentiation" as used herein denotes that the tumor cells as defined herein are induced for neuronal differentiation by the indicated cell culture conditions, time and cell culture medium. Said priming of the tumor cells for neuronal differentiation can be carried out, for example, by cultivation in an appropriate cell culture medium, and, optionally, by reduction of serum in the cell culture medium and/or the addition of retinoic acid. As known to those skilled in the art, a differentiation status of the tumor cells in which said tumor cells are "induced for neuronal differentiation" or "primed for neuronal differentiation" is characterized by, e.g., the expression of neuronal induction markers as set forth elsewhere herein. As evident to those skilled in the art, said "primed" or "induced" differentiation status of the tumor cells does, however, not yet represent the final neuronal differentiation status of the tumor cells which is defined by the characteristics as set forth elsewhere herein, but a previous differentiation step in the neuronal differentiation lineage. Only after having carried out step b) of the differentiation method of the invention, the tumor cells are finally differentiated, i.e. neuronal differentiated cells as specified herein. Cultivation of the tumor cells as defined herein in a culture medium under conditions and for a time which primes said tumor cells for neuronal differentiation means cultivating said tumor cells in an appropriate cell culture medium for 12 hours to 7 days at 37° C., preferably 24 hours to 6 days, more preferably 36 hours to 5 days and is known in the art. Appropriate cell culture media which can be used for priming said tumor cells for neuronal differentiation (also referred to herein as "priming medium") include, for instance, OptiMEM, MEMalpha, RPMI-1640, Minimal essential medium (MEM), Ham's F12 medium, Dulbeccos modified Eagle's Medium (DMEM) or DMEM:F12 (1:1). The priming medium can comprise further components known in the art, such as serum (e.g. FBS), NEAA, retinoic acid, growth factors (such as NGF or FGF), vitamins, fatty acids, hormones and/or antibiotics. An appropriate cell culture medium for priming SiMa cells for neuronal differentiation comprises, for example, 80 to 98.6% OptiMEM, 1 to 7.5% FBS, 0.2 to 5% B27 supplement, 0.2 to 5% N2 supplement, and, optionally, 0.1 to 2.5% non-essential amino acids (NEAA).

Advantageously, it has been found by the present inventors that a cell culture medium comprising 92.5% OPTI-MEM®, 5% FBS, 1% non-essential amino acids, 1% B-27 supplement and 0.5% N-2 supplement is particularly suitable for the priming of SiMa cells, as shown in the following Example. For priming SiMa cells for neuronal differentiation, the preferred cultivation period is 12 hours to 5 days. Preferably, the priming of SiMa cells is carried out under cell culture conditions as shown, in the following Example. For priming of P19 cells, for example, 90 to 99.8% MEM-alpha, 0.2 to 10% FBS, and 0.001 to 10 micromolar ($\mu$M) retinoic acid (RA), preferably 0.1 $\mu$M RA, can be utilized. Here, the cultivation period is preferably 3 days to 7 days.

The term "differentiation medium" as used in step b) of the method for the generation of neurotoxin-sensitive, neuronal differentiated cells of the invention is a cell culture medium having an osmolality of 100 to 270 mOsm/kg. Preferably, the osmolality of the differentiation medium is between 120 to 250 mOsm/kg, more preferably between 150 and 240 mOsm/kg, even more preferably between 180 mOsm/kg and 230 mOsm/kg, most preferably between 200 and 225 mOsm/kg and most preferred about 225 mOsm/kg. As set forth elsewhere herein and in the following Example, the present inventors have surprisingly found that the low osmolality of the differentiation medium is responsible for the increased sensitivity to BoNT of the neurotoxin-sensitive, neuronal differentiated cells produced by the method of the invention. As a differentiation medium, for example, neurobasal medium, MEM, DMEM:F12 or any basal medium known in the art can be used if adapted to the appropriate osmolality, e.g., by reduction of the NaCl concentration in the media formulation or by dilution of the media with water. Further, the differentiation medium comprises at least one supplement. The supplement can be (i) B27 supplement, (ii) N2 supplement, (iii) NS21 supplement, or (iv) combinations thereof. For example, B27 supplement can be used in combination with N2 supplement. B27 supplement is known in the art and generally used for growth and maintenance of neurons. Furthermore, B27 supplement is commercially available, e.g., from Life Technologies. Typically, B27 supplement can be used in a concentration of 0.2% to 5% in the method of the invention. N2 supplement (which can be obtained from, e.g., Life Technologies) is a chemically defined, serum-free supplement based on Bottenstein's N-1 formulation. N2 Supplement is recommended for growth and expression of neuroblastomas as well as post-mitotic neurons in primary cultures from both the peripheral nervous system (PNS) and the central nervous system (CNS). N2 supplement can be used in a concentration of 0.2% to 5% in the method of the invention. NS21 supplement is a re-defined and modified B27 supplement in which 21 different ingredients have been used for neuronal cultures, as described, for example, in the publication by Chen et al. (2008), Journal of Neuroscience Methods 171, 239-247. Typically, NS21 supplement is used in a concentration of 0.2% to 5% in the method of the invention. Further ingredients used in the above-referenced differentiation medium comprise Glutamine or GlutaMax, one or more antibiotic agents, NEAA, FBS (0.1 to 20%), GT1b (0.1 to 300 $\mu$M), retinoic acid (RA) (1 nanomolar (nM) to 300 $\mu$M), growth factors (such as 100 ng/ml NGF, 40 ng/ml BDNF, 40 ng/ml CNTF, 5 ng/ml LIF, 5 ng/ml GDNF, TGF or FGF) or further differentiation factors known in the art (1% DMSO, 1 mM Dibutyryl cAMP, 1 mM Butyrate, 5 $\mu$g/ml celecoxib, Y-27632, SB431542, sonic hedgehog (SHH) etc.). The cells of step b) of this method of the invention are cultivated in said differentiation medium preferably for at least 3 days in order to obtain neurotoxin-sensitive, neuronal differentiated cells. Cultivation can also be longer, for example, for at least 3.5 days, 4 days, 4.5 days, 5 days, 6 days, 7 days (1 week), 8 days, 9 days, 10 days, 11 days, 12 days, 13 days, 14 days (2 weeks), 15 days, 16 days, 17 days, 18 days, 19 days, 20 days, 21 days (3 weeks) or even longer. Preferred is cultivation of P19 tumor cells for 2 to 3 weeks, and cultivation of SiMa cells for 3 days to 7 days. Preferred differentiation media and cell culture conditions which allow for the neuronal differentiation are shown in the following Example. Preferably, said neuronal differentiated cells represent finally differentiated neuronal cells as defined elsewhere herein.

The term "osmolality" as used herein means the measure of solute concentration, which can be defined as the number of osmoles (Osm) of solute per kilogram (kg) of solution (osmol/kg or Osm/kg). The osmolality of a solution is usually expressed as Osm/kg. Osmolality measures the number of osmoles of solute particles per unit mass of solution. Osmolarity is a measure of the osmoles of solute per liter of solvent (osmol/l or Osm/l). Osmolality and osmolarity can be determined on an osmometer.

In a further aspect, the aforementioned method of the invention can comprise additional steps. For example, said additional steps can encompass steps for determining the biological activity of a neurotoxin polypeptide as defined herein. To this end, the neurotoxin-sensitive, neuronal differentiated cells obtained or obtainable by the methods of the invention are first brought in contact with a neurotoxin polypeptide. The term "contacting" as used in accordance with the methods of the invention refers to bringing the aforementioned cells and the neurotoxin in physical proximity as to allow physical and/or chemical and/or biological interaction. The neurotoxin can be comprised by a sample, preferably a biological sample such as a cell, cell lysate, blood, plasma, serum or lymph fluid. Suitable conditions which allow for specific interaction are well known to the skilled worker. Said conditions will depend on the cells and neurotoxins to be applied in the methods of the present invention, and can be adapted by the skilled artisan without further ado. Moreover, a time being sufficient to allow interaction can also be determined by the skilled worker by routine experimentation. For example, a specific amount of an isolated or recombinant neurotoxin polypeptide or a variant thereof as defined herein or a sample comprising a neurotoxin polypeptide can be added to the neurotoxin-sensitive, neuronal differentiated cells. Thereafter, the cells are incubated with the neurotoxin polypeptide for at least 24 h, preferably 48 h, more preferably for 72 h under conditions which allow for the neurotoxin polypeptide to exert its biological activity. "Conditions which allow for the neurotoxin polypeptide to exert its biological activity" as used herein are known in the art. Subsequently, the cells are stopped, for example by the addition of lysis buffer, and the biological activity of the neurotoxin polypeptide is determined as shown, for instance, in the following Example.

The term "neurotoxin", "neurotoxin polypeptide" or "neurotoxin protein" as used in the present invention refers to the seven distinct serotypes of Botulinum neurotoxins, i.e. BoNT/A, BoNT/B, BoNT/C1, BoNT/D, BoNT/E, BoNT/F, BoNT/G, and to Tetanus Neurotoxin (TeNT), and variants thereof as defined herein. The corresponding nucleic acid and amino acid sequences are known in the art; see, e.g., Uniprot or TREMBL sequence database. Preferably, BoNT/A is used in the methods of the invention (WO 2009/114748). The corresponding receptors and substrates for said neurotoxins have been referred to elsewhere herein. The neurotoxin polypeptide can be a naturally occurring neurotoxin or a non-naturally occurring neurotoxin. A naturally occurring neurotoxin polypeptide is produced by a naturally occurring process, including, for example, isoforms produced from a post-translational modification, an alternatively-spliced transcript or a spontaneous mutation and subtypes. For instance, BoNT/A subtypes are BoNT/A1 subtype, BoNT/A2 subtype, BoNT/A3 subtype, BoNT/A4 subtype or BoNT/A5 subtype. A naturally occurring neurotoxin polypeptide includes the above-referenced sequences in which 1, 2, 3, 4, 5, 6, 7, 8, 9, 10, 20, 30, 40, 50, 100 or more amino acid residues are added, substituted or deleted. Commercially available pharmaceutical compositions which comprise a naturally-occurring BoNT/A have already been mentioned in the introductory part. A non-naturally occurring neurotoxin polypeptide means any neurotoxin polypeptide whose structure was modified with the aid of human manipulation, including, for example, a neurotoxin polypeptide with an altered amino acid sequence produced by genetic engineering using random mutagenesis or rational design and a neurotoxin polypeptide generated by chemical synthesis. Such non-naturally occurring neurotoxin polypeptides have been described in the art.

In another aspect of the invention, the neurotoxin polypeptide has an amino acid sequence being at least 40%, at least 50%, at least 60%, at least 70%, at least 75%, at least 80%, at least 85%, at least 90%, at least 95%, at least 98% or at least 99% identical to the amino acid sequence of BoNT/A, BoNT/B, BoNT/C1, BoNT/D, BoNT/E, BoNT/F, BoNT/G, or Tetanus neurotoxin as defined herein. Identical as used in the present invention refers to sequence identity of amino acid sequences wherein the sequences are aligned so that the highest order match is obtained. This can be achieved by using published techniques or methods codified in computer programs such as, for example, BLASTP, BLASTN, FASTA, Altschul 1990, J. Mol. Biol. 215, 403. The percent identity values are, in one aspect, calculated over the entire amino acid sequence. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (1987, J. Mol. Evolution 25, 351; Higgins 1989 CABIOS 5, 151) or the programs Gap and BestFit (Needleman and Wunsch 1970, J Mol Biol 48; 443; Smith and Waterman 1981, Adv. Appl. Math. 2, 482), which are part of the GCG software packet (Genetics Computer Group 1991, 575 Science Drive, Madison, Wis., USA 53711), are to be used. The sequence identity values recited above in percent (%) are to be determined, in one aspect of the invention, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. It will be understood that the aforementioned variants shall, in an aspect of the invention, retain, at least one of the biological properties of neurotoxins and, in an aspect, all of the biological properties of a neurotoxin polypeptide recited herein. In a further aspect, the variants can be neurotoxins having improved or altered biological properties, e.g., they may comprise cleavage sites which are improved for enzyme recognition or may be improved for receptor binding or any other property specified above.

The neurotoxins referred to herein, in principle, comprise an N-terminal light chain and a C-terminal heavy chain. The neurotoxins are produced as single chain precursor molecules, referred to as "unprocessed neurotoxin polypeptides". As a result of the subsequent processing, "processed neurotoxin polypeptide" is obtained. The said processed neurotoxin polypeptide exhibits the biological properties characteristic for a neurotoxin, namely, (a) receptor binding, (b) internalization, (c) translocation across the endosomal membrane into the cytosol, and/or (d) endoproteolytic cleavage of proteins involved in synaptic vesicle membrane fusion. Therefore, the processed neurotoxin polypeptide is referred to as biologically active or mature neurotoxin polypeptide. The biological activity of the neurotoxin polypeptides, in an aspect, results from all of the aforementioned biological properties, as set forth elsewhere herein.

In another aspect, the neurotoxin polypeptide in accordance with the method of the invention may be a chimeric molecule. Said chimeric molecule, in one aspect, may have single domains substituted. Accordingly, in another aspect, the portion of the neurotoxin heavy chain is replaced by a portion of an Fc domain of an antibody.

The term "amount" as used herein encompasses the absolute amount of, e.g., a neurotoxin polypeptide, the relative amount or the concentration of the said polypeptide as well as any value or parameter which correlates thereto or can be derived there from.

The term "determining the amount" of, e.g., a neurotoxin polypeptide relates to measuring the absolute amount, relative amount or concentration of, e.g., the neurotoxin polypeptide in a quantitative or semi-quantitative manner. Suitable measures for detection are well known to those skilled in the art. It will be understood that the determination of the amount of neurotoxin polypeptides, in an aspect, also requires calibration of the method by applying standard solutions with predefined amounts of neurotoxin polypeptides. It is well known to those skilled in the art how to carry out such a calibration.

The term "determining the biological activity of a neurotoxin polypeptide" as used herein means measuring the biological activity of a neurotoxin protein, namely, (a) receptor binding, (b) internalization, (c) translocation across the endosomal membrane into the cytosol, and/or (d) endoproteolytic cleavage of proteins involved in synaptic vesicle membrane fusion. More specifically, the overall cellular mechanisms whereby a neurotoxin (e.g., BoNT/A) cleaves a neurotoxin substrate (e.g., SNAP-25) encompasses the binding of the neurotoxin to its corresponding receptor (e.g., binding of BoNT/A to BoNT/A receptor), the internalization of the neurotoxin/receptor complex, the translocation of the neurotoxin light chain from an intracellular vesicle into the cytoplasm and the proteolytic cleavage of the neurotoxin substrate. In vitro and in vivo assays for determining the biological activity of a neurotoxin polypeptide are well known in the art and have been mentioned elsewhere herein (see, e.g., Pellett et al., Withemarsh et al Toxicol. Sciences 126(2), 426-435 (2012), WO 2010/105234 A1).

As used herein, the term "sensitivity to neurotoxin (polypeptide) activity" refers to the lowest dose that an assay can measure consistently above the signal detected by a non-treatment control or background signal.

In one aspect of the method of the invention, the differentiation medium as used in step b) of the aforementioned method of the invention further comprises retinoic acid. Preferably, said retinoic acid is present in the neurobasal medium in a concentration of between 0.01 micromolar (μM) and 300 μM. More preferably, retinoic acid is present in a concentration of between 0.1 and 0.5 μM retinoic acid for P19 tumor cells, i.e. in a concentration of 0.1, 0.2, 0.3, 0.4 or 0.5 μM retinoic acid; and between 1 and 5 μM for SiMa cells, i.e. in a concentration of 1, 2, 3, 4, or 5 μM, most preferably in a concentration of 3 μM. Retinoic acid is a known neural inducer which is able to induce differentiation of neuronal cells, including neuroblastoma cells. The addition of low concentrations of retinoic acid into the differentiation medium used in step b) of the method of the invention has been found to enhance advantageously the sensitivity of the tumor cells to neurotoxin polypeptides.

In a further aspect of the method of the invention, said differentiation medium in step b) further comprises an antibiotic agent and/or a cytostatic agent which inhibits growth of non-neuronal cells. As antibiotic agent, for example, penicillin-streptomycin can be used. As a cytostatic agent, for instance, cytosine-1-ß-D-arabinofuranoside (AraC) can be used. The addition of an antibiotic agent prevents the growth of bacteria in the cell culture medium, whereas the cytostatic agent inhibits cell growth and multiplication of non-tumor/non-neuronal cells which could otherwise overgrow the tumor cells in the differentiation method of the present invention.

In still another aspect of the method of the invention, said differentiation medium in step b) further comprises GT1b. GT1b is a ganglioside which binds to neurotoxin and potentially mediates the selectivity of neurotoxins for neurons. Accordingly, GT1b can be used as an enhancer for the BoNT uptake into the tumor cells in the methods of the invention. Preferably, said GT1b is present in a concentration of between 25 and 75 μM, i.e. in a concentration of 25 μM, 30 μM, 35 μM, 40 μM, 45 μM, 50 μM, 55 μM, 60 μM, 65 μM, 70 μM or 75 μM, more preferably in a concentration of 50 μM.

In yet another aspect of the method of the invention, step a) of said method of the invention comprises cell culture conditions comprising reduction of serum from the (cell) culture medium and/or addition of retinoic acid. "Reduction of serum from the culture medium" as used herein means, for example, stepwise reduction of serum, e.g., at an interval of 2 to 5 days, from 10% to 5% to 2.5% to 1% to 0%. Alternatively, serum-containing cell culture medium can be replaced by serum-free cell culture medium, in one step. The removal of growth factors contained in the serum allows for the differentiation of the tumor cells as defined herein. In addition or alternatively, retinoic acid can be added to the culture medium in low concentrations as set forth elsewhere herein.

In some aspects of the method of the invention, said tumor cells which are able to differentiate into neuronal cells are SiMa cells available, e.g., from DSMZ (German collection of Microorganisms and Cell cultures) under the ACC deposit number: 164. The SiMa cell line DSMZ ACC 164 is also known as parental SiMa cell line. SiMa cells as used in the methods of the invention can be parental SiMa cells or (sub)clones thereof. Such subclones are also known in the art; see, e.g., WO 2010/105234, U.S. Pat. No. 8,476,068 B2 or Ester Fernández-Salas, Joanne Wang, Yanira Molina, Jeremy B. Nelson, Birgitte P. S. Jacky, K. Roger Aoki—PloSOne; 2012 7(11) e49516.

SiMa cells can be cultivated according to the protocol of the DMSZ. In an aspect, cultivating SiMa cells in a cell culture medium under conditions and for a time which primes said SiMa cells for neuronal differentiation in step a) of the method of the invention comprises cultivation of said SiMa cells in a cell culture (or growth) medium comprising at least OptiMEM, FBS, B27 supplement, N2 supplement and, optionally NEAA, for at least 12 hours (h), at least 24 hours or preferably at least 36 hours at 37° C.

In an aspect of the method of the invention, the culture or priming medium for SiMa cells in step a) comprises 80% to 98.8% OptiMEM, 1 to 10% FBS, 0.2 to 5% B27 supplement and/or 0.2 to 5% N2 supplement. Optionally, said culture medium for SiMa cells further comprises non-essential amino acids and/or an antibiotic and/or retinoic acid.

Preferably, the culture or priming medium for SiMa cells in step a) comprises 92.5% OptiMEM, 5% FBS, 1% B27 supplement, 0.5% N2 supplement and 1% NEAA.

In an aspect of the method of the invention, the differentiation medium in step b) comprises a medium having an osmolality of 100 to 270 mOsm/kg. Preferably, said medium is neurobasal medium used in a concentration of 86 to 98.8%. The differentiation medium can further comprise one or more of the following ingredients: 0.2 to 5% B27 supplement and/or 0.2 to 5% N2 supplement; 0.5 to 2% non-essential amino acids (NEAA); 1 to 5 μM retinoic acid; 0.5 to 2% GlutaMAX and/or 25 to 75 μM GT1b.

Preferably, the differentiation medium in step b) comprises 97% neurobasal medium, 2% B27 supplement, 1% GlutaMAX, and 3 μM retinoic acid.

In an aspect of the method of the invention, the SiMa cells are cultivated in step a) for at least 36 hours.

In an aspect of the method of the invention, the SiMa cells are cultivated in step a) on tissue culture dishes which are coated with at least one compound selected from the group consisting of: poly-L-lysine, poly-D-lysine, collagen, laminins, and gelatine. Coating of cell culture dishes is well known to those skilled in the art. Preferably, the tissue culture dishes are coated with poly-L-lysine.

The present invention provides for a novel differentiation protocol with which a significant increase in the sensitivity of SiMa cells to neurotoxin polypeptides can be achieved. In addition, said test system is more precise and robust than tests for the biological activity of neurotoxin polypeptide described in the art. In a first step for priming the SiMa cells for neuronal differentiation, the SiMa cells were cultivated in a novel priming medium comprising 92.5% Opti-MEM®, 5% FBS, 1% B27 supplement, 0.5% N2 supplement and 1% NEAA. If applicable, one or more antibiotic agents were also be added to the cell culture medium. The cells were then seeded on coated multi-well plates. Optimal results have been achieved with cell culture dishes which were coated with poly-L-lysine. Alternatively, collagen, poly-D-lysine, laminins, gelatin, or combinations thereof can also be used for the coating of the cell culture dishes. After at least 36 h growth of the seeded cells in the above-referenced growth culture or priming medium, said medium has been substituted by six different differentiation media, in comparison. After three to seven days of differentiation in which the differentiation medium has been replaced by fresh differentiation medium, if applicable, neurotoxin polypeptide (as exemplified by BoNT/A) was added to the differentiation medium. After further 75 h of incubation, the cells were stopped and analyzed for biological activity of the added neurotoxin polypeptide. In comparison, differentiation media with low osmolality delivered the best results: The use of a differentiation medium comprising neurobasal medium containing 2% B27 supplement, 1% GlutaMAX and 3 µM retinoic acid provided EC50 values of 0.22 pM. Said differentiation medium had an osmolality of about 225 mOsm/kg. A similar result of an EC50 value of 0.24 pM was found for a differentiation medium comprising MEM, 2% B27 supplement, 1% N2 supplement, and 3 µM retinoic acid, diluted to about 225 mOsm/kg. The comparatively simple differentiation protocol of the present invention allows for high reproducibility and high sensitivity (EC50 below 0.3 pM; LLOD below 0.1 pM), which allows for high dilutions of the sample to be analyzed. Accordingly, the sensitivity of SiMa cells which have been generated by the differentiation method of the present invention is preferably, less than 10 pM, less than 5 pM, less than 2 pM, less than 1 pM, less than 0.5 pM or even less than 0.3 pM.

In other aspects of the method of the invention, said tumor cells which are able to differentiate into neuronal cells are P19 cells which can be obtained, e.g., from DSMZ under the ACC deposit number: 316, from ATCC under CRL-1825 or from ECACC under 95102107. P19 cells can be cultivated according to the protocol of the DSMZ. In an aspect, cultivating the P19 cells in a cell culture medium under conditions and for a time which primes said P19 cells for neuronal differentiation in step a) of the method of the invention comprises cultivation of said P19 tumor cells on bacteriological petri dishes in a cell culture (or growth) medium comprising at least MEM-alpha and FBS for at least 3 days, 4 days or preferably 5 days such that cell aggregates are formed. In an aspect, said cell culture medium for P19 cells comprises retinoic acid, preferably in a concentration of between 75 and 125 nM, more preferably 100 nM. In an aspect, the cell culture medium comprises 95% MEM-alpha, 5% FBS and 0.1 µM retinoic acid. Preferably, the P19 cell aggregates are harvested and isolated cells primed for neuronal differentiation are generated from the aggregates by protease treatment, e.g. trypsin treatment. In an aspect of the method of the invention, the P19 cells in step b) of the method of the invention are cultivated for 2 to 3 weeks in differentiation medium with low osmolality as defined herein, preferably neurobasal medium with an osmolality of about 225 mOsm/kg.

The present invention provides for a novel differentiation protocol for P19 cells with which a significant increase in the sensitivity of the cells towards BoNT could be achieved, as demonstrated in the following Example. In the differentiation protocol of the invention, P19 cells were cultured as described in the prior art. For priming the P19 cells for neuronal differentiation, the cells were seeded on petri dishes used for bacteria (i.e. no cell culture dishes) and 100 nM retinoic acid was added. After five days, the resulting cell aggregates were isolated and trypsinized. Thereafter, the cells were seeded on multi-well plates and cultivated further. It has surprisingly been found by the present inventors that the use of neurobasal medium (neurobasal medium comprising 2% B27 supplement, 1% N2 supplement and 1% GlutaMAX) as well as the addition of low concentrations of retinoic acid (100 nM) could increase the sensitivity of the cells towards BoNT further. The growth of non-neuronal cells could be inhibited by the addition of a cytostatic drug (for example, 5 µM AraC). Moreover, it has been found that the addition of GT1b enhances the uptake of BoNT of the cells when GT1b is added to the medium upon intoxication of the cells with BoNT. To this end, for example, 50 µM GT1b has been used. After two to three weeks of differentiation, in which the medium has been replaced if necessary, BoNT was added to the cell culture medium. After 72 h of incubation with BoNT, the cells were stopped and analyzed by methods shown in the following Example.

As exemplified for two different cell lines, the present invention provides for a novel cell-based test system for the determination of the biological activity of neurotoxins. Said cell-based test system of the invention is extremely sensitive and robust and provides an alternative to conventional animal tests. Furthermore, the cell-based test system of the invention is a simple differentiation protocol, in comparison to cell-based test systems described in the art and allows for high reproducibility and high sensitivity (EC50 below 0.1 pM for SiMa cells, and below 1 pM for P19 cells) which allows for high dilutions of the neurotoxin-containing samples to be analyzed. Such high dilutions of the samples is extremely important as regards excipients or impurities contained in the sample to be analyzed in order to apply said potentially disturbing substances in concentrations as low as possible. Finally, the cell-based test system of the invention is more flexible and economic than systems described in the prior art.

It is to be understood that the definitions and explanations of the terms made above apply mutatis mutandis for all aspects described in this specification in the following except as otherwise indicated.

The invention further relates to a neurotoxin-sensitive, neuronal differentiated cell obtainable or obtained by the method of the invention. Preferably, in case SiMa cells are used, said cells have an EC50 value of less than 10 pM, less than 5 pM, less than 2 pM, less than 1 pM, less than 0.5 pM or even less than 0.3 pM. It is also preferred that the sensitivity for Botulinum neurotoxins of neuronal differentiated SiMa cells generated by the differentiation method of the invention is increased at least 1.5 fold, at least 2 fold, at least 3 fold, at least 4 fold, at least 5 fold, at least 6 fold, at least 7 fold, at least 8 fold, at least 9 fold or even at least 10 fold, in comparison to SiMa cells differentiated in a differentiation medium having an osmolality of about 290 to 350 mOsm/kg which is used commonly, in neuronal differentiation processes described in the art. Similar results could be achieved using P19 cells; see Example.

In addition, the invention provides for a method for determining the activity of a neurotoxin polypeptide comprising the steps of:

a) contacting the neurotoxin-sensitive, neuronal differentiated cells, preferably obtainable or obtained by the method of the invention, with a neurotoxin polypeptide;

b) cultivating the neurotoxin-sensitive, neuronal differentiated cells of step a) for 3 to 74 hours or preferably 72 hours under conditions which allow for the neurotoxin polypeptide to exert its biological activity; and c) determining the biological activity of the neurotoxin polypeptide in the said cells after cultivation according to step b).

Specifically, said method for determining the activity of a neurotoxin polypeptide comprises the steps of:

a) cultivating tumor cells which are able to differentiate into neuronal cells in a culture medium under conditions and for a time which primes said tumor cells for neuronal differentiation;

b) cultivating the tumor cells primed for neuronal differentiation of step a) in a differentiation medium having an osmolality of 100 to 270 mOsm/kg, and comprising (i) B27 supplement and/or (ii) N2 supplement, for at least 3 days, thereby obtaining neurotoxin-sensitive, neuronal differentiated cells;

c) contacting the neurotoxin-sensitive, neuronal differentiated cells of step b) with a neurotoxin polypeptide;

d) cultivating the neurotoxin-sensitive, neuronal differentiated cells of step c) for 3 to 74 hours, or preferably 72 hours, under conditions which allow for the neurotoxin polypeptide to exert its biological activity; and e) determining the biological activity of the neurotoxin polypeptide in the said cells after cultivation according to step d).

The determination of the biological activity of the neurotoxin polypeptide can be carried out by methods described in the art (see, e.g., Pellett et al., Withemarsh et al. Toxicological Sciences 126(2),426-435 (2012), WO 2010/105234 A1, WO 2009/114748, WO 2012/123370, WO 2013/131991). Preferably, the tumor cells which are able to differentiate into neuronal cells are SiMa cells, more preferably parental SiMa cells (DSMZ ACC 164). The neurotoxin polypeptide is preferably BoNT/A.

The invention pertains also to the use of a cell culture medium and/or differentiation medium as specified in the method of the invention for generating neurotoxin-sensitive, neuronal differentiated cells ex vivo from neuronal differentiated cells, preferably neuroblastoma cells.

In a further aspect, the invention provides for a cell culture or priming medium comprising 80 to 98.8% OptiMEM, 1 to 10% FBS, 0.2 to 5% B27 supplement and/or 0.2 to 5% N2 supplement. Alternatively, 0.2 to 5% NS21 supplement can be used. Preferably, said medium comprises 93.5% OptiMEM, 5% FBS, 1% B27 supplement and 0.5% N2 supplement. Said medium is particularly useful for priming SiMa cells. Opti-MEM® reduced serum media (Life Technologies) is a modification of Eagle's Minimum Essential Media, buffered with HEPES and sodium bicarbonate and supplemented with hypoxanthine, thymidine, sodium pyruvate, L-glutamine, trace elements and growth factors. The culture medium can in an aspect further comprise an antibiotic agent as defined herein and/or non-essential amino acids (NEAA). Said culture medium of the invention is particularly useful in step a) of the method for generation of neurotoxin-sensitive, neuronal differentiated cells of the invention using SiMa cells.

Finally, the invention relates to a kit adapted for carrying out the aforementioned methods, said kit comprising a cell culture medium comprising 80 to 98.8% OptiMEM, 1 to 10% FBS, 0.2 to 5% B27 supplement and/or 0.2 to 5% N2 supplement and, optionally, non-essential amino acids and/or an antibiotic, and SiMa cells. Preferably, said cell culture medium comprises 93.5% OptiMEM, 5% FBS, 1% B27 supplement and 0.5% N2 supplement, and SiMa cells. The kit can further comprise a differentiation medium as defined herein having an osmolality of 100 to 270 mOsm/kg, preferably neurobasal medium, and at least one supplement as indicated herein, i.e. B27, N2 or NS21 supplement. Preferably, said differentiation medium comprises 78 to 98.3% neurobasal medium, 1 to 10% FBS, 0.5 to 2% GlutaMAX, 0.2 to 5% B27 supplement, and/or 0.2 to 5% N2 supplement. Further preferred media which can be used in the kit of the invention are shown in the following Example.

It is to be understood that the kit of the present invention is to be used for practicing the methods referred to herein above. In one aspect, it is envisaged that all components are provided in a ready-to-use manner for practicing the methods referred to above. In a further aspect, the kit contains instructions for carrying out the said methods. The instructions can be provided by a user manual in paper- or electronic form. For example, the manual may comprise instructions for interpreting the results obtained when carrying out the aforementioned methods using the kit of the present invention.

All references cited in this specification are herewith incorporated by reference with respect to their entire disclosure content and the disclosure content specifically mentioned in this specification.

Abbreviations as used herein:

OptiMEM: Opti-MEM® reduced serum media (Life Technologies) is a modification of Eagle's Minimum Essential Media, buffered with HEPES and sodium bicarbonate and supplemented with hypoxanthine, thymidine, sodium pyruvate, L-glutamine, trace elements and growth factors. Most cells grown in serum-supplemented media can be transferred to Opti-MEM® with a minimum of 50% reduction in serum.

FBS: Fetal bovine serum is the most widely used serum-supplement for the in vitro cell culture of eukaryotic cells. FBS is commercially available from many manufacturers, such as Sigma-Aldrich, Invitrogen, Life Technologies and others.

B27 supplement: B27 supplement is generally used for growth and maintenance of neurons. B27 supplement is commercially available as 50× or 100× stock solutions, e.g., from Life Technologies.

N2 supplement: Commercially obtainable as 50× or 100× stock solutions, e.g., from Life Technologies. N2 supplement is recommended for growth and expression of neuroblastomas as well as post-mitotic neurons in primary cultures from both the peripheral nervous system and the central nervous system. N2 supplement can be used as a substitute for Bottenstein's N1 formulation. N2 supplement can be used with neurobasal media supplemented with growth factors such as bFGF or EGF or used with DMEM.

NS21 supplement: NS21 supplement is a re-defined and modified B27 supplement in which 21 different ingredients have been used for neuronal cultures, as described, for example, in the publication by Chen et al. (2008), Journal of Neuroscience Methods 171, 239-247.

NEAA: Non-essential amino acids cell culture supplement commercially available by many manufacturers such as Invitrogen or Cyagen is usually provided as a stock solution containing several kinds of non-essential amino acids such as glycine, L-alanine, L-asparagine, L-glutamic acid, L-aspartic acid, L-serine or L-proline. It is used as a supplement to cell culture media for optimized cell growth.

P19 cells: P19 cells are embryonic carcinoma cell lines derived from an embryo-derived teratocarcinoma in mice. The cell line is multipotent cells which can differentiate into all three germ layers cell types. Also, it is the most characterized embryonic carcinoma (EC) cell line that can be specific induced into cardiac muscle cells and neuronal cells by different specific treatment. Exposing aggregated P19 cells to dimethyl sulfoxide (DMSO) can let differentiate into cardiac and skeletal muscle. Also, exposing P19 cells to retinoic acid (RA) can differentiate them into neuronal cells (McBurney & Rogers (1982), *Dev. Biol* 89(2):503-508; Rudnicki, et al. (1990) *Dev. Biol* 138(2):348-358).

SiMa cells: SiMa cells correspond to a neuroblastoma (Nb) cell line, carrying the major recurrent chromosome changes associated with poor prognosis Nb, including amplification of N-MYC by formation of double minutes (dmin), der(1)(1;17)(p35;q12) and der(22)t(17;22)(q22; p13), and loss of chromosome 11, documented at both initiation and late passage. In contrast to these cytogenetic stigmata of poor prognosis, analysis of catecholamine synthesis by high pressure liquid chromatography (HPLC) measurement revealed an advanced degree of adrenergic differentiation with high rates of 3,4-Dihydroxyphenylalanine (DOPA), noradrenaline, homovanillic acid (HVA), and vanillylmandelic acid (VMA) production. Contrastingly advanced differentiation and poor prognostic genetic markers combine to render SiMa a unique instrument for investigating the pathology and therapy of Nb (Marini et al., Cancer Genet. Cytogenet. (1999), 112:161-4).

MEM-alpha: Minimal Essential Medium Alpha (Invitrogen, Life Technologies)

Neurobasal medium: Neurobasal® Medium (Invitrogen, Life Technologies) is a basal medium that meets the special cell culture requirements of pre-natal and embryonic neuronal cells when used with GIBCO® B-27® Supplement. Neurobasal® Medium can be used to grow neuronal cells from hippocampus, cortex and other regions of the brain. Neurobasal® Medium allows for both long and short term maintenance of homogeneous populations of neuronal cells without the need of an astrocyte feeder layer.

GlutaMax: GIBCO® GlutaMAX™ media is a cell culture media which contains a stabilized form dipeptide from L-glutamine, L-alanyl-L-glutamine, that prevents degradation and ammonia build-up even during long-term cultures. Extremely stable in aqueous solution, the L-alanyl-L-glutamine dipeptide will not degrade into ammonia in storage or incubation like L-glutamine.

The invention will now be illustrated by the following Example which shall, however, not be construed as limiting the scope of the present invention.

EXAMPLE

The influence of differences between Neurobasal and MEM medium on the Botulinum Neurotoxin (BoNT) sensitivity i) SiMa parental cells were cultivated according to the protocol of the DSMZ (German collection of Microorganisms and Cell cultures). One day before plating the cells on 96-well plates, the medium was changed to 92.5% OPTI-MEM® (Gibco by Life Technologies™ #51985)+5% FBS (PAA # A15-152)+1% non-essential amino acids (NEAA; Gibco by Life Technologies™ #11140-038)+1% B-27 supplement (Gibco by Life Technologies™ #17504-044)+ 0.5% N-2 supplement (Gibco by Life Technologies™ #17502-048) as "priming medium. Cells (30.000 cells/cm$^2$) were plated on 96-well plates (TPP #92096) five days before addition of Botulinum Neurotoxin (BoNT) in the above mentioned priming medium. 24 h after plating the cells, the medium was exchanged for one of the following differentiation media:

1. 97% Neurobasal (Gibco by Life Technologies™ #21103)+2% B-27 supplement (Gibco by Life Technologies™ #17504-044)+1% GlutaMAX™ (Gibco by Life Technologies™ #35050-038)+3 µM retinoic acid (RA; Sigma-Aldrich # R2625) or
2. 96% MEM (Gibco by Life Technologies™ #42360)+2% B-27 supplement (see above)+1% N-2 supplement (see above)+1% NEAA (see above)+3 µM RA (see above) or
3. 96% MEM (see above)+2% B-27 supplement (see above)+1% N-2 supplement (see above)+1% NEAA (see above)+3 µM RA (see above)+Vitamin B12+Fe+Zn (low) or
4. 96% MEM (see above)+2% B-27 supplement (see above)+1% N-2 supplement (see above)+1% NEAA (see above)+3 µM RA (see above)+Vitamin B12+Fe+Zn (high) or
5. 96% MEM (see above)+2% B-27 supplement (see above)+1% N-2 supplement (see above)+1% NEAA (see above)+3 µM RA (see above); diluted to 225 mOsm/kg or
6. 97% Neurobasal (see above)+2% B-27 supplement (see above)+1% GlutaMAX™ (see above)+3 µM retinoic acid (see above)+Zn (high)

Four days after the change to differentiation medium, half of the medium per well is exchanged for fresh medium which contains BoNT/A in different concentrations (serial 1:2 dilution in 11 steps starting from 10 pM plus negative control without BoNT/A). 72 h after addition of BoNT, the medium was aspirated and lysis buffer containing 0 was added. The plate was incubated at room temperature (RT) and then Roti-load 1 (Roth # K929.1) was added. Samples prepared as aforementioned could be stored at a temperature below −70° C. The low temperature is critical because SNAP-25 seems to be specifically degraded at higher temperatures of storage. After that the samples were separated using SDS-PAGE and subsequently analyzed by Western blot. The EC50 was determined and the values were compared in Table 1 (the average of 4 experiments is given).

TABLE 1

| Differentiation medium | EC50 [pM] | EC50 [mol/l] |
|---|---|---|
| 1. Neurobasal + B-27 + GlutaMax + RA | 0.22 | 2.18 × 10$^{-13}$ |
| 2. MEM + B-27 + NEAA + N-2 + RA | 1.51 | 1.51 × 10$^{-12}$ |
| 3. MEM + B-27 + NEAA + N-2 + RA + B12 + Fe + Zn (low) | 2.14 | 2.14 × 10$^{-12}$ |
| 4. MEM + B-27 + NEAA + N-2 + RA + B12 + Fe + Zn (high) | 1.51 | 1.51 × 10$^{-12}$ |
| 5. MEM + B-27 + NEAA + N-2 + RA, diluted to 225 mOsm/kg | 0.24 | 2.37 × 10$^{-13}$ |
| 6. Neurobasal + B-27 + GlutaMax + RA + Zn (high) | 0.27 | 2.65 × 10$^{-13}$ |

Bold EC50 values = high sensitivity for BoNT

Surprisingly, the sensitivity of the cells to BoNT/A was increased by 10-fold just by substituting MEM by Neurobasal medium (2. vs. 1.). Supplementing MEM with components of Neurobasal medium which MEM lacks (iron, vitamin B12 and zink) did not affect the susceptibility of the cells to BoNT/A (2. vs. 3. and 4.). Diluting MEM with sterile deionized water to 225 mOsm/kg, however, yielded the same surprising effect as the use of Neurobasal medium. Thus, reducing the osmolality from 300 mOsm/kg to 225 mOsm/kg dramatically increased the sensitivity of SiMa cells from ~2 pM to ~0.2 pM.

Table 2 shows the osmolality values of differentiation media 1 to 6.

TABLE 2

Osmolality of the tested differentiation media

| Differentiation medium | Composition | Osmolality (mOsm/kg) |
|---|---|---|
| 1 | Neurobasal + B-27 + GlutaMax + RA | 225 |
| 2 | MEM + B-27 + NEAA + N-2 + RA | 300 |
| 3 | MEM + B-27 + NEAA + N-2 + RA + B12 + Fe + Zn (low) | 300 |
| 4 | MEM + B-27 + NEAA + N-2 + RA + B12 + Fe + Zn (high) | 300 |
| 5 | MEM + B-27 + NEAA + N-2 + RA, diluted to 225 mOsm/kg | 225 |
| 6 | Neurobasal + B-27 + GlutaMax + RA + Zn (high) | 225 |

For example, MEM has an osmolality of about 300 mOsm/kg. Usually, cell culture media used in the prior art have an osmolality between 290 and 350 mOsm/kg. The osmolality of the cell culture media is not essentially influenced by other ingredients. For supplements, an osmolality within the desired range is chosen.

ii) P19 cells were cultivated according to the protocol of the DSMZ (German collection of Microorganisms and Cell cultures). 5 days before plating the cells on 96-well plates, the cells were transferred onto bacterial grade petri dishes and the medium was changed to 95% MEM-alpha (Gibco by Life Technologies™ #32571) supplemented with 5% FBS (PAA # A15-152) and 0.1 µM retinoic acid (RA; Sigma-Aldrich # R2625) as "priming medium". During 5 days of growth the cells formed clumps or aggregates. Those were trypsinized and the cells (30.000 cells/cm$^2$) were plated on 96-well plates (TPP #92096) five days before addition of Botulinum Neurotoxin (BoNT) in the above mentioned priming medium. 24 h after plating the cells, the medium was exchanged for one of the following differentiation media:

1. 97% Neurobasal (Gibco by Life Technologies™ #21103)+2% B-27 supplement (Gibco by Life Technologies™ #17504-044)+1% GlutaMAX™ (Gibco by Life Technologies™ #35050-038)+3 µM retinoic acid (RA; Sigma-Aldrich # R2625); 225 mOsm/kg.
2. 95% MEM-alpha (Gibco by Life Technologies™ #32571)+5% FBS (PAA # A15-152)+0.1 µM retinoic acid (RA; Sigma-Aldrich # R2625); 300 mOsm/kg.
3. 90% MEM-alpha (Gibco by Life Technologies™ #32571)+10% FBS (PAA # A15-152); 300 mOsm/kg.
4. 97% MEM-alpha (Gibco by Life Technologies™ #32571)+2% B-27 supplement (see above)+1% N-2 supplement (see above)+1% NEAA (see above)+1 µM retinoic acid (RA; Sigma-Aldrich # R2625); 300 mOsm/kg.

Four days after the change to differentiation medium, half of the medium per well is exchanged for fresh medium which contains BoNT/A in different concentrations (serial 1:2 dilution in 11 steps starting from 10 pM plus negative control without BoNT/A). 72 h after addition of BoNT, the medium was aspirated and lysis buffer containing benzonase was added. The plate was incubated at room temperature (RT) and then Roti-load 1 (Roth # K929.1) was added. Samples prepared as aforementioned could be stored at a temperature below −70° C. The low temperature is critical because SNAP-25 seems to be specifically degraded at higher temperatures of storage. After that the samples were separated using SDS-PAGE and subsequently analyzed by Western blot. The EC50 was determined and the values were compared in Table 3 (the average of 4 experiments is given).

TABLE 3

| Differentiation medium | EC50 [pM] | EC50 [mol/l] |
|---|---|---|
| 1. Neurobasal + B-27 + GlutaMax + RA | 1.10 | 1.10 × 10$^{-12}$ |
| 2. α-MEM + 5% FBS + RA | 8.84 | 8.84 × 10$^{-12}$ |
| 3. α-MEM + 10% FBS | 17.7 | 1.77 × 10$^{-11}$ |
| 4. α-MEM + B-27 + NEAA + N-2 + RA | 12.5 | 1.25 × 10$^{-11}$ |

Bold EC50 values = high sensitivity for BoNT

The invention claimed is:

1. A method for determining the activity of a neurotoxin polypeptide comprising the steps of:
   a) cultivating SiMa or P19 tumor cells in a culture medium comprising 80 to 98.8% OptiMEM, 1 to 10% Fetal Bovine Serum (FBS), 0.2 to 5% B27 supplement and/or 0.2 to 5% N2 supplement and, optionally, non-essential amino acids and/or an antibiotic under conditions and for a period of time which primes SiMa or P19 tumor cells for neuronal differentiation;
   b) adjusting the osmolality of a differentiation medium comprising 78 to 98.3% neurobasal medium, 1 to 10% FBS, 0.5 to 2% GlutaMAX, 0.2 to 5% B27 supplement, and/or 0.2 to 5% N2 supplement, to an osmolality of 180 to 230 mOsm/kg; and
   c) cultivating the SiMa or P19 tumor cells primed for neuronal differentiation in step a) for at least 3 days in the differentiation medium of step b) having an osmolality of 180 to 230 mOsm/kg;
   d) contacting the neurotoxin-sensitive, neuronal differentiated cells of step c) with a neurotoxin polypeptide;
   e) cultivating the neurotoxin-sensitive, neuronal differentiated cells of step d) for 3 to 74 hours under conditions which allow for the neurotoxin polypeptide to exert its biological activity; and
   f) determining the biological activity of the neurotoxin polypeptide in the cells after cultivation according to step e).

2. The method of claim 1, wherein the differentiation medium further comprises retinoic acid.

3. The method of claim 2, wherein the retinoic acid is present in a concentration of between 0.01 µM and 300 µM.

4. The method of claim 1, wherein the differentiation medium further comprises an antibiotic agent and/or a cytostatic agent which inhibits growth of non-neuronal cells.

5. The method of claim 1, wherein the differentiation medium further comprises ganglioside GT1b (GT1b).

6. The method of claim 5, wherein the GT1b is present in a concentration of between 25 µM and 75 µM or is present in a concentration of 50 µM.

7. The method of claim 1, wherein the osmolality of the differentiation medium is about 225 mOsm/kg.

8. The method of claim 1, wherein step a) comprises reduction of serum from the culture medium and/or addition of retinoic acid.

9. The method of claim 1, wherein the tumor cells are SiMa cells (DSMZ ACC deposit number: 164).

10. The method of claim 9, wherein the SiMa or P19 tumor cells are cultivated in step a) on tissue culture dishes which are coated with at least one compound selected from the group consisting of poly-L-lysine, poly-D-lysine, collagen, laminins, and gelatin.

11. The method of claim 1, wherein the tumor cells are P19 cells (DSMZ ACC deposit number: 316).

12. The method of claim 1, wherein the SiMa or P19 tumor cells are cultivated in step a) for a period of at least 36 hours.

13. The method of claim 1, wherein the culture medium in step a) further comprises an antibiotic agent and/or non-essential amino acids (NEAA).

\* \* \* \* \*

UNITED STATES PATENT AND TRADEMARK OFFICE
CERTIFICATE OF CORRECTION

PATENT NO. : 10,781,421 B2  
APPLICATION NO. : 16/144059  
DATED : September 22, 2020  
INVENTOR(S) : Karl-Heinz Eisele and Kai Harting Page 1 of 1

It is certified that error appears in the above-identified patent and that said Letters Patent is hereby corrected as shown below:

On the Title Page

Column 1, Assignee: "MERE" should read -- MERZ --

Signed and Sealed this  
Seventeenth Day of November, 2020

Andrei Iancu  
*Director of the United States Patent and Trademark Office*